(12) United States Patent  (10) Patent No.: US 7,578,837 B2
Arnold et al.  (45) Date of Patent: *Aug. 25, 2009

(54) WARMING APPARATUS WITH AN INFLATABLE COVER AND AN INLET PORT PLUG

(75) Inventors: Randall C. Arnold, Minnetonka, MN (US); Scott D. Augustine, Bloomington, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/818,721

(22) Filed: Jun. 15, 2007

(65) Prior Publication Data

US 2007/0255363 A1  Nov. 1, 2007

Related U.S. Application Data

(60) Division of application No. 09/815,877, filed on Mar. 23, 2001, now Pat. No. 7,244,268, which is a continuation of application No. 09/496,599, filed on Feb. 2, 2000, now Pat. No. 6,228,107, which is a continuation of application No. 09/368,206, filed on Aug. 4, 1999, now Pat. No. 6,241,755, which is a continuation of application No. 08/624,101, filed on Mar. 29, 1996, now Pat. No. 5,997,572.

(51) Int. Cl.
*A61F 7/00* (2006.01)
(52) U.S. Cl. ....................... 607/104; 607/108
(58) Field of Classification Search ............... 607/104, 607/108
See application file for complete search history.

(56) References Cited

U.S. PATENT DOCUMENTS

| 730,378 | A | 6/1903 | Lambert |
| 3,829,918 | A | 8/1974 | Stamberger |
| 3,978,530 | A | 9/1976 | Amarantos |
| 4,043,474 | A | 8/1977 | McCord ................... 215/211 |
| D246,698 | S | 12/1977 | Morris ..................... D9/284 |
| 4,086,670 | A | 5/1978 | Krause et al. |
| 4,572,188 | A | 2/1986 | Augustine et al. ......... 128/380 |
| 4,787,875 | A | 11/1988 | Baron et al. ............. 446/226 |
| 4,892,219 | A | 1/1990 | Smith ...................... 220/287 |
| 4,930,174 | A | 6/1990 | Hunter |
| 5,000,663 | A | 3/1991 | Gorton |
| 5,027,999 | A | 7/1991 | Kucherer ................. 229/125 |
| 5,075,910 | A | 12/1991 | Morten |
| 5,125,238 | A | 6/1992 | Ragan et al. ............ 62/259.3 |
| 5,176,387 | A | 1/1993 | Taggart ................... 294/8.6 |
| 5,304,213 | A | 4/1994 | Berke et al. .............. 607/104 |
| 5,360,439 | A | 11/1994 | Dickerhoff et al. ......... 607/104 |
| 5,405,371 | A | 4/1995 | Augustine et al. .......... 607/107 |
| 5,486,205 | A | 1/1996 | Cornell et al. ............. 607/104 |
| 5,489,062 | A | 2/1996 | Wagner et al. ......... 229/117.18 |
| 5,545,194 | A | 8/1996 | Augustine ................ 607/104 |

(Continued)

OTHER PUBLICATIONS

McGraw-Hill Dictionary of Scientific and Technical Terms, Fifth Edition, 1994, definitions for "plug" and "snap".

(Continued)

*Primary Examiner*—Lee S Cohen
(74) *Attorney, Agent, or Firm*—Terrance A. Meador; INCAPLAW

(57) ABSTRACT

An apparatus for warming a person includes an inflatable cover having two inlet ports and a plug removably received in one of the ports. With the plug received in the one port, the cover can be inflated by way of the port without the plug.

10 Claims, 9 Drawing Sheets

U.S. PATENT DOCUMENTS

| | | | |
|---|---|---|---|
| 5,632,769 A * | 5/1997 | Kappel et al. | 607/104 |
| 5,656,283 A | 8/1997 | Brummer et al. | 424/433 |
| 5,716,387 A | 2/1998 | Kappel et al. | 607/107 |
| 5,728,145 A | 3/1998 | Phlipot et al. | 607/104 |
| 5,944,214 A | 8/1999 | Conti et al. | 220/304 |
| 5,997,572 A | 12/1999 | Arnold et al. | 607/104 |
| 6,228,107 B1 | 5/2001 | Arnold et al. | 607/104 |
| 6,241,755 B1 | 6/2001 | Arnold et al. | 607/104 |
| 6,309,408 B1 | 10/2001 | Arnold et al. | 607/104 |
| 7,244,268 B2 * | 7/2007 | Arnold et al. | 607/104 |
| 2001/0012957 A1 | 8/2001 | Arnold et al. | 607/104 |

OTHER PUBLICATIONS

Webster's New Collegiate Dictionary, 1974, definitions for "plug" and "snap".

Decision on Appeal, Appeal 2006-1521, U.S. Appl. No. 09/815,877, Technology Center 3700, Decided: Oct. 16, 2006.

United States Court of Appeals for the Federal Circuit 98-1001, *Augustine Medical, Inc.*, v. *Gaymar Industries, Inc., and Medisearch P R, Inc., and Mallinckrodt Group, Inc., and Mallinckrodt Medical, Inc.*, pp. 1-11.

* cited by examiner

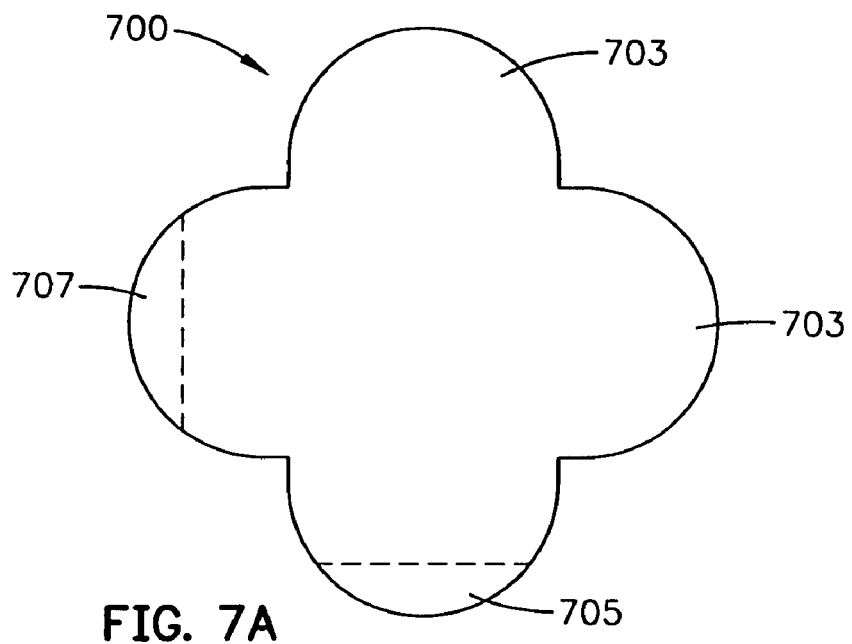
FIG. 7A
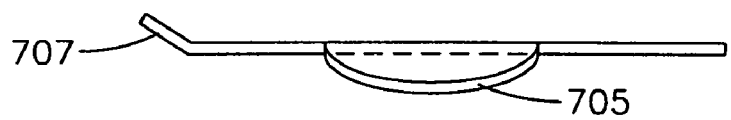
FIG. 7B
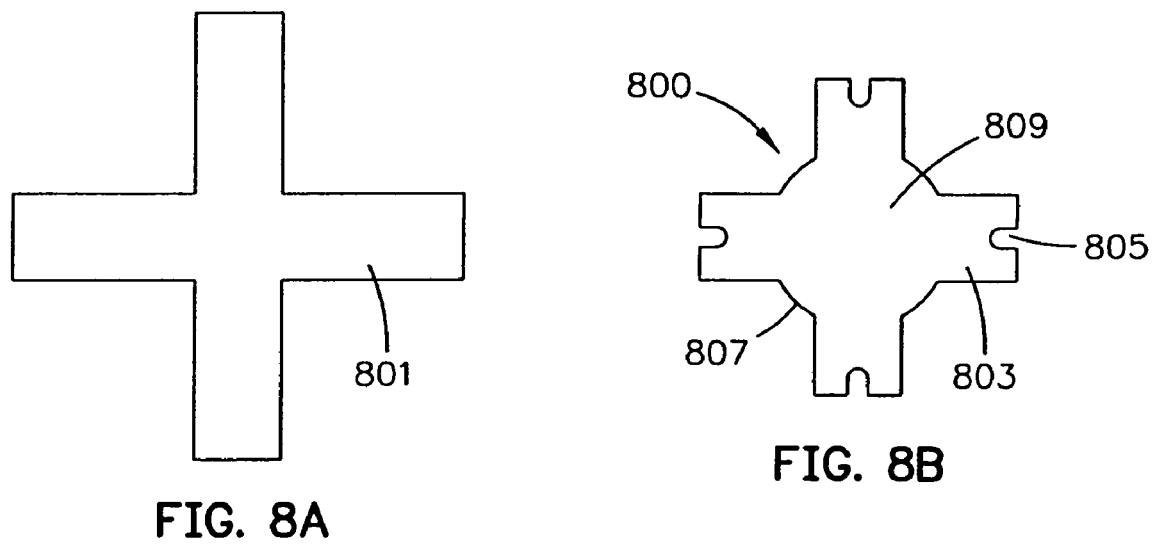
FIG. 8A
FIG. 8B

WARMING APPARATUS WITH AN INFLATABLE COVER AND AN INLET PORT PLUG

PRIORITY

This is a divisional of U.S. patent application Ser. No. 09/815,877, filed Mar. 23, 2001 now U.S. Pat. No. 7,244,268, which is a continuation of U.S. patent application Ser. No. 09/496,599, filed Feb. 2, 2000, now U.S. Pat. No. 6,228,107, which is a continuation of U.S. patent application Ser. No. 09/368,206, filed Aug. 4, 1999, now U.S. Pat. No. 6,241,755, which is a continuation of U.S. patent application Ser. No. 08/624,101, filed Mar. 29, 1996 now U.S. Pat. No. 5,997,572.

BACKGROUND OF THE INVENTION

1. Field of the Invention

The present invention relates to devices for warming a patient during a medical procedure, and more particularly, to an apparatus for restricting air flow through an inlet port in an inflatable thermal blanket used to warm a patient during a medical procedure.

2. Description of the Related Art

Hypothermia, a condition in which a person's body temperature drops below normal, presents serious potential consequences to a patient. Studies have shown that hypothermia occurs in nearly 75 percent of all patients who undergo surgical procedures. Based on recent numbers, this means that 14 million patients a year in the United States alone suffer from hypothermia during surgical procedures. Hypothermia during surgery may be caused by anesthesia, air conditioning within the operating room, infusion of cold blood, I.V. solutions, and/or irrigation fluids, in addition to other factors.

One well known method for reducing hypothermia during surgical procedures is to place an inflatable thermal blanket over a patient during a surgical procedure. The thermal blanket is inflated with a warmed airstream, exhausting warmed inflating air onto the patient. An inflatable thermal blanket was first disclosed in U.S. Pat. No. 4,572,188 assigned to Arizant Healthcare Inc., the assignee of the present application. U.S. Pat. No. 5,405,371, also assigned to Arizant Healthcare Inc., is directed to an inflatable thermal blanket that extends transversely across the arms and chest of a patient's body, and is for use during surgery at or below the patient's chest. These patents disclosed an airstream inlet: In later products, the airstream inlet port comprises a cardboard structure adhesively attached to the surface of the thermal blanket. A hole provided through the inlet port is sized to accept the end or nozzle of an inflation hose. In some thermal blankets, a plurality of inlet ports is provided to allow an inflation hose to be attached at any one of a plurality of locations on the blanket. When an operator inserts the inflation hose into an inlet port, the port is closed about the hose. The surface material of the thermal blanket which coincides with the inlet port is either removed or perforated in order to allow a warmed airstream to pass from the hose through the port to the interior of the thermal blanket. The warmed airstream enters the thermal blanket and is forced out a plurality of small exhaust holes in the lower surface of the thermal blanket. Typically, the user perforates or removes that portion of the thermal blanket which covers an inlet port only when that port is to be used. Accordingly, each of the unused inlet ports remains sealed until after the first use.

One problem with this design is that if the operator decides in the middle of the procedure to move the inflation hose from one inlet port to another, the first port must be resealed or otherwise closed in order to prevent air from exiting through that port instead of through the holes on the lower surface of the blanket, as intended. A number of means have been used to reseal or close an inlet port after removal of an inflation hose. However, none of these means are completely satisfactory. For example, tape has been used to seal an open port, but is generally a nuisance to apply. The prior art suggests many other means and modes for sealing or closing an open port, including: adhesive strips, double sided tape, snaps, zippers, folding flaps, Ziplock®-type seal, hook and loop fastener strips, folding wire, or plastic bars. Each of these methods has a number of drawbacks. The method is either relatively costly, or it is inconvenient, requiring a great deal of attention or time of an operator, possibly during critical moments. Such methods and means require accommodation in manufacture of a thermal blanket, increasing production costs and decreasing manufacturability.

Accordingly, it would be desirable to provide a method and apparatus for closing inlet ports in an inflatable thermal blanket such that the port may be opened and closed conveniently and repeatedly.

SUMMARY OF THE INVENTION

An apparatus to warm a person includes an inflatable cover that can be disposed on a portion of the person's body. Two inlet ports are provided in the inflatable cover and a plug is removably received in at least one port of the two ports. The plug may have a planar central body and a plurality of extensions that are coplanar with the central body and which extend from the central body, at least two of which are receivable in the one port.

Alternatively, the plug includes a flange, a substantially vertical ring-like wall receivable in the one port, and at least two protuberances which extend from the substantially vertical ring-like wall to resist removal of the plug from the one port.

BRIEF DESCRIPTION OF THE DRAWINGS

FIG. 7a is an illustration of an embodiment of the invention having a distal end of an appendage tilted up ward.

FIG. 7b is a side view of the embodiment of FIG. 7a.

FIG. 8a-8e illustrates a number of alternative embodiments of the invention having varied appendages.

FIG. 10 is a side view of the embodiment of FIG. 9a.

Like reference numbers and designations in the various drawings refer to like elements.

DETAILED DESCRIPTION OF THE PREFERRED EMBODIMENTS

Throughout this description, the preferred embodiment and examples shown should be considered as exemplars, rather than as limitations on the present invention.

Overview

Figure 1:
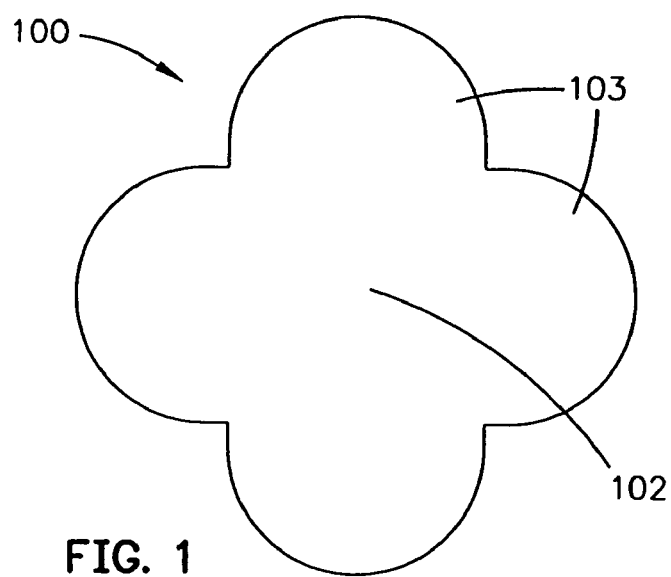
FIG. 1 is an illustration of the preferred embodiment of the present invention
Figure 2:
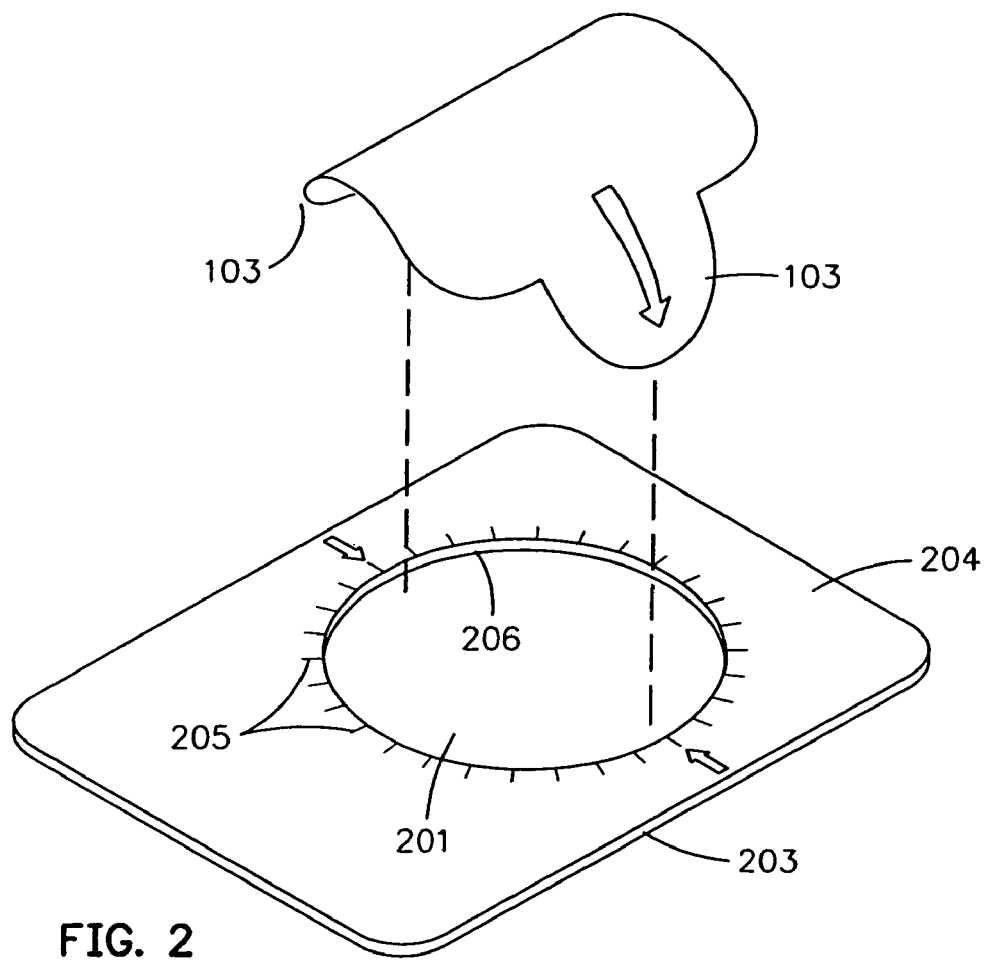
FIG. 2 is an illustration of the preferred embodiment of the present invention immediately before insertion into an inlet port.
Figure 3:
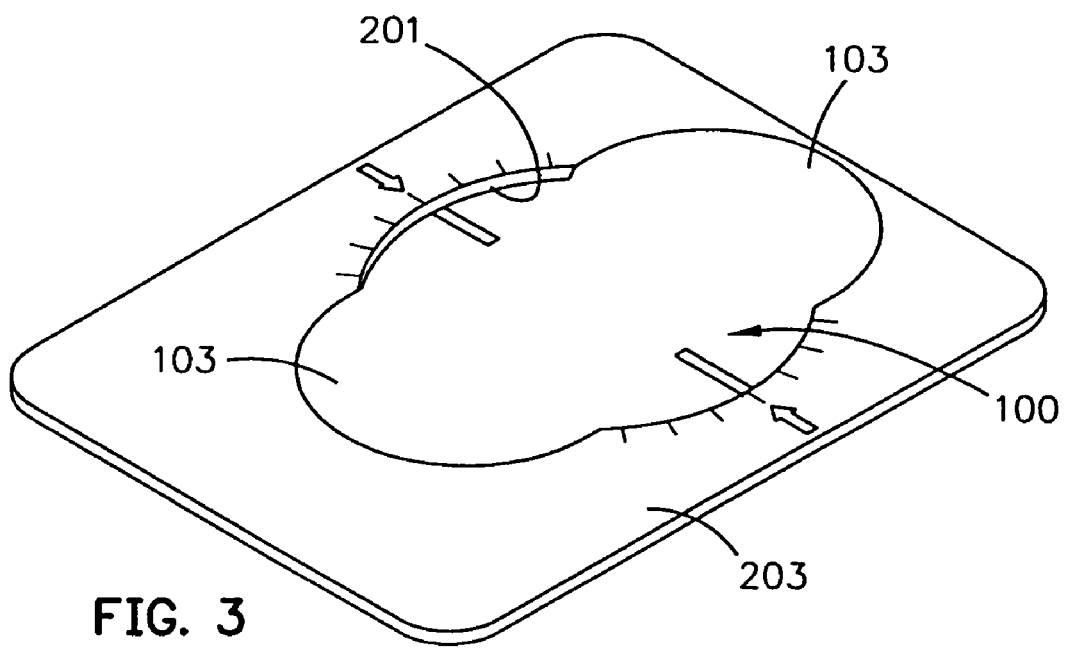
FIG. 3 is an illustration of the preferred embodiment of the present invention after insertion into an inlet port.
Figure 4:
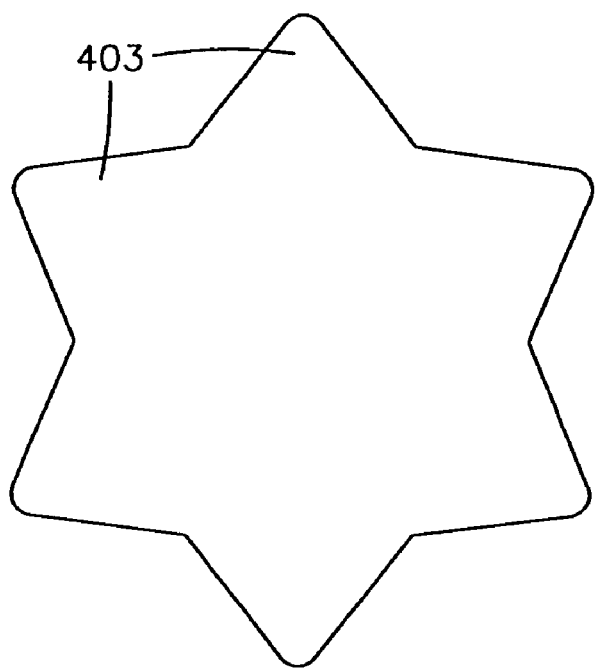
FIG. 4 is an illustration of an alternative embodiment of the present invention.
Figure 5:
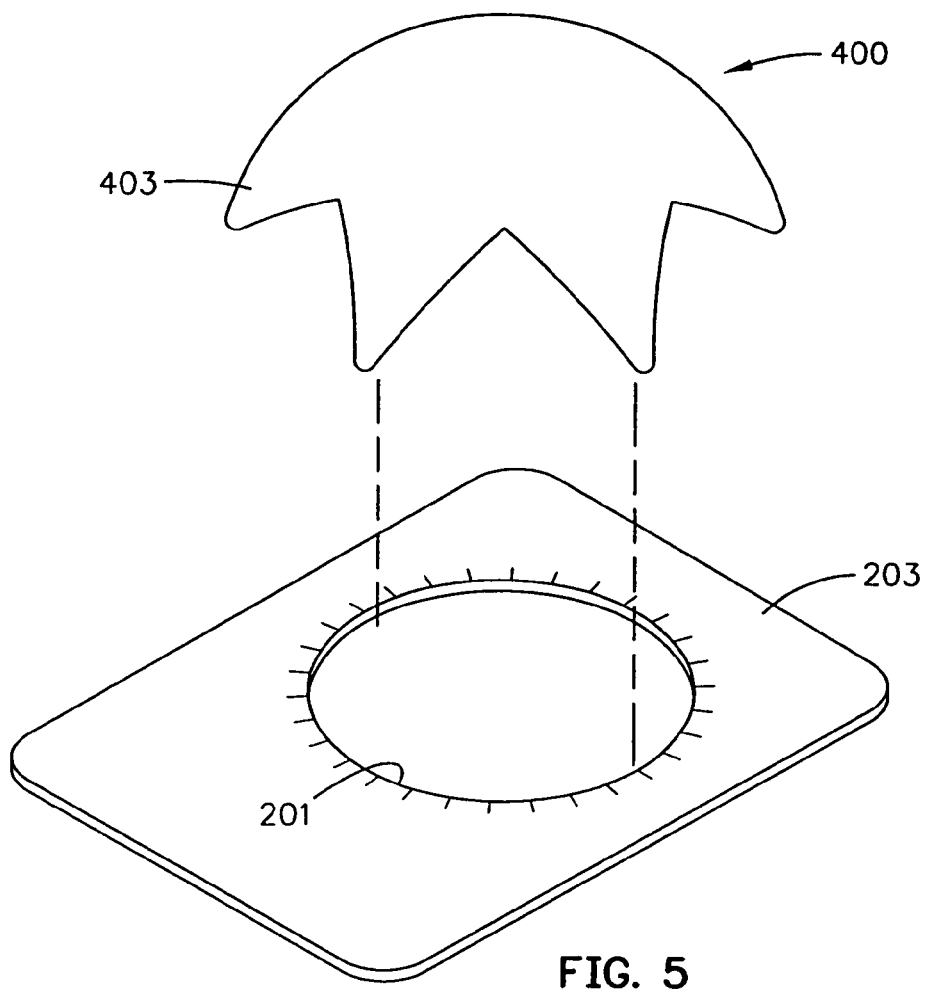
FIG. 5 is an illustration of the alternative embodiment of FIG. 4 immediately before insertion into an inlet port.
Figure 6:
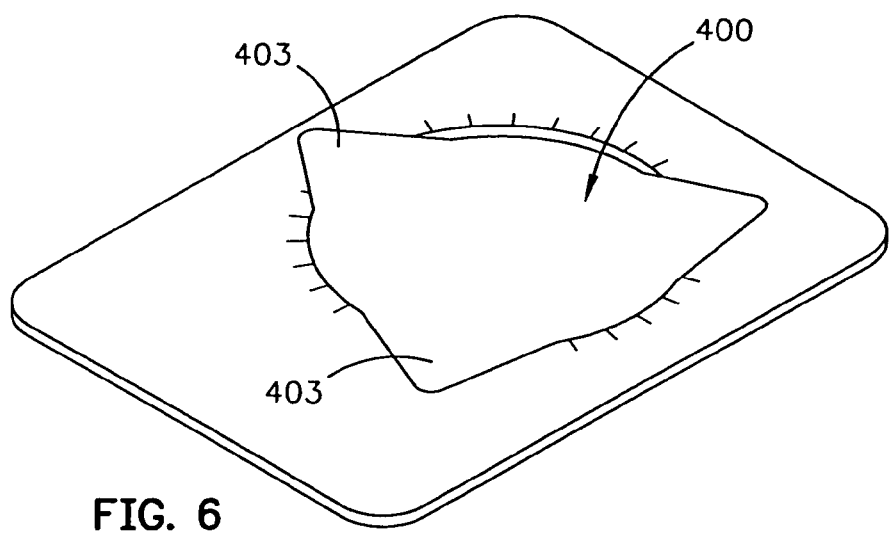
FIG. 6 is an illustration of the alternative embodiment of FIG. 4 after insertion into an inlet port.

The present invention is a plug for removably closing an inlet port of an inflatable thermal blanket. One preferred embodiment of the present invention is shown in FIGS. 1-3. As shown FIG. 1, the plug has a central body 102 that is essential circular and has a diameter equal to that of an inlet port with which the invention is to be used. Extending preferably radially outward from the central body 102 are a plurality of extensions 103. In this embodiment of the present invention, an even number of opposing extensions are provided, as shown in FIGS. 1-8. These extensions 103 may be substantially curved, or rounded, like the leaves of a 4-leaf clover. Alternatively, the extensions may be generally pointed, as shown in FIGS. 4-6. Preferably four extensions 103 are provided. However, fewer than four extensions may be provided or, as shown in FIG. 4, more than four extensions 403 may be provided. The number of extensions is generally unrelated to the shape of each of the extensions. In accordance with the preferred invention, the plug is made of a generally flexible, resilient sheet of material, such as plastic or a wood pulp product, such as paper or cardboard. Preferably, the material is rigid enough to allow bending along a central axis through the center of the plug in predominantly one direction at a time. The material is preferably die-cut into the desired shape. Alternatively, the material may be stamped, extruded, molded or otherwise formed into the desired shape.

In accordance with one method of the present invention, the plug is bent such that outer edges of opposing extensions may be inserted into an inlet port 201 (see FIG. 2). The inlet port is typically a circular hole through a rectangular sheet 203 of cardboard. The sheet has a first (or, outer) surface 204, and a second (or, inner) surface indicated by reference numeral 206. Slits 205 about the perimeter of the port 201 allow the port to accommodate an end or nozzle of an inflation hose (not shown) which is slightly larger in outside diameter than the inner diameter of the port. As shown in FIGS. 3 and 6, when the plug 100 is released, the plug flattens across and substantially, if not entirely closes the port 201. The plug is retained in the port by the extensions that engage the second (or, inner) surface of the sheet 203. Preferably an equal number of extensions 103, 403 are placed inside the port 201 as remain outside the port although this is not vital to the practice of the invention.

Figure 8C:
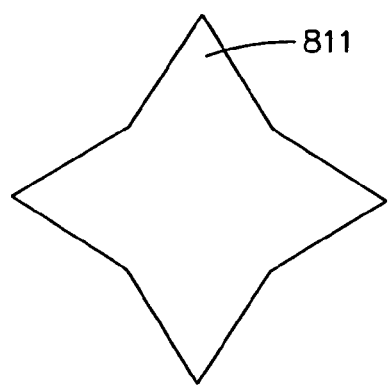
Figure 8D:
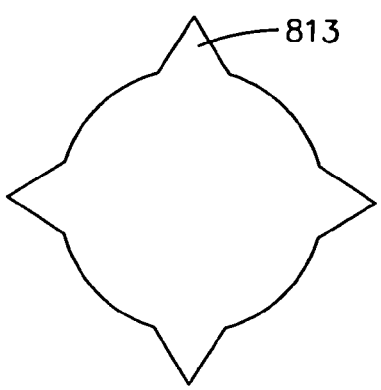
Figure 8E:
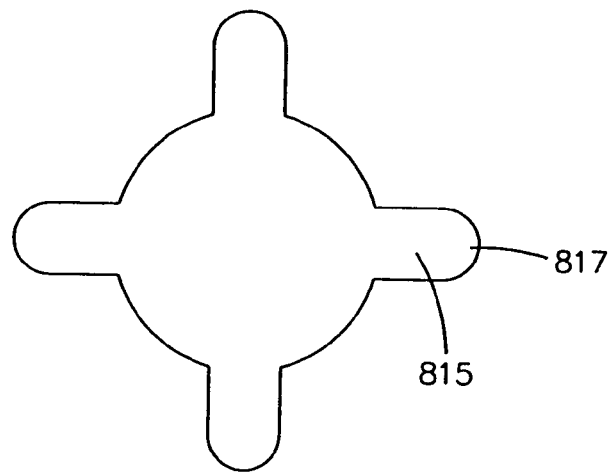

In an alternative embodiment of the present invention shown in FIGS. 7a and 7b, the distal end of one or more of the extensions may be formed at an angle to allow the plug 700 to be more easily removed from the port 201. Similarly, the distal end 705 of one or more extensions 703 may be formed at a slight angle downward to allow the present invention to be more easily inserted into a port 201. It will be clear to those of ordinary skill in the art, that a number of alternative shapes may be used, as shown in FIGS. 8a-8e. FIG. 8a shows the present invention formed as a cross. Accordingly, each of the extensions 801 are essentially rectangular. As shown in FIG. 8b, the present invention has extensions 803 which are notched at the distal end 805. As shown in FIG. 8b, the width of each extension 803 is less than the diameter of a central circular body 809 divided by the square root of 2. Accordingly, a portion 807 of the perimeter of the central circular body 809 forms a part of the perimeter of the plug 800. FIG. 8c illustrates an embodiment of the present invention in which four generally triangular shaped extensions 811 are provided. FIG. 8d illustrates an embodiment in which four relatively smaller generally triangular extensions 813 are provided. FIG. 8e illustrates an embodiment of the present invention in which extensions 815 are generally rectangular having rounded distal ends 817. It will be clear to those skilled in the art that numerous other shapes and configurations are possible. Those illustrated in FIGS. 1 through 8 are merely provided as exemplars.

Figure 9A:
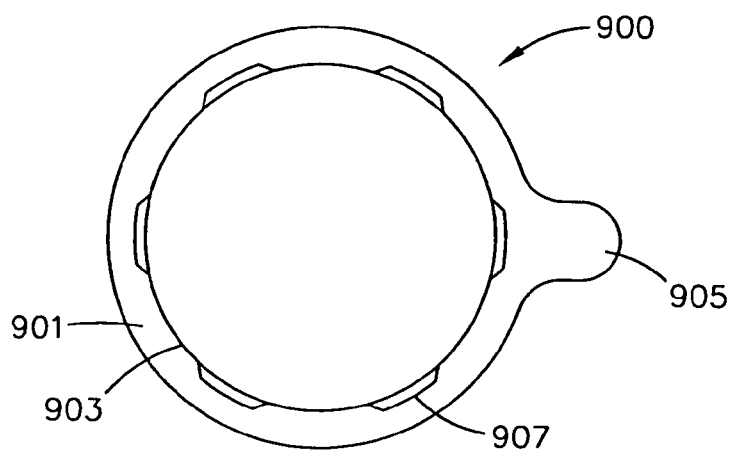
FIG. 9a is an illustration of an embodiment of the invention having protuberances.

FIG. 9a illustrates yet another embodiment of the present invention. The plug 900 in FIG. 9a may be vacuum-formed from a sheet of plastic. The plug 900 preferably has a flange 901 which is larger in diameter than inlet port 201 with which the plug 900 is to be used. The flange prevents the plug 900 from passing completely though the port 201. The invention has a generally vertical ring-like wall 903 that press fits into the inlet port 201. Accordingly, the diameter of the wall 903 is essentially equal to the diameter of the port 201 with which the plug 900 is to be used. The flange 901 preferably has a tab 905 which extends therefrom. The tab 905 provides the user with a handle to grasp when removing the plug 900 from a port 201.

Protruding from the wall 903 are a plurality of protuberances 907 which extend radially outward from the wall 903. Each protuberance 907 has an upper and lower slope 909, 911, respectively. The upper and lower slopes 909, 911 allow the plug 900 to be inserted and removed relatively easily, while resisting removal of the plug 900 from the port 201, such that the plug 900 is retained under normal conditions but may be easily removed when desired.

In accordance with one embodiment of the present invention, the flange 901 is sufficiently thick to allow the user to comfortably grasp the plug 900 when the plug 900 is filly inserted into an insertion port 201. For example, in one embodiment, the flange 901 is approximately 0.25 inches thick.

Figure 9B:
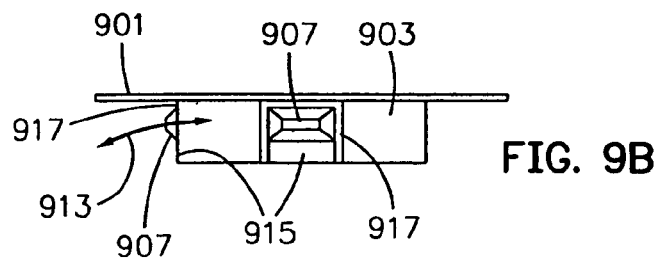
FIG. 9b is a side view of an embodiment of the invention having retractable protuberances.
Figure 10:
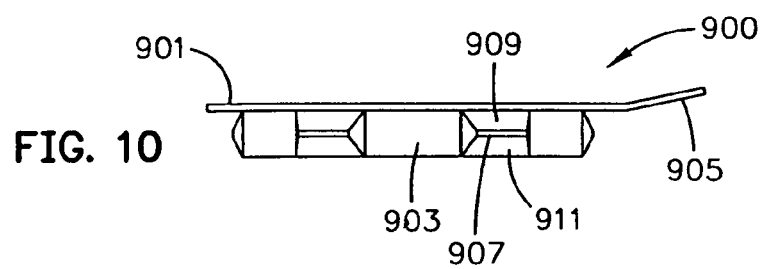
Figure 11:
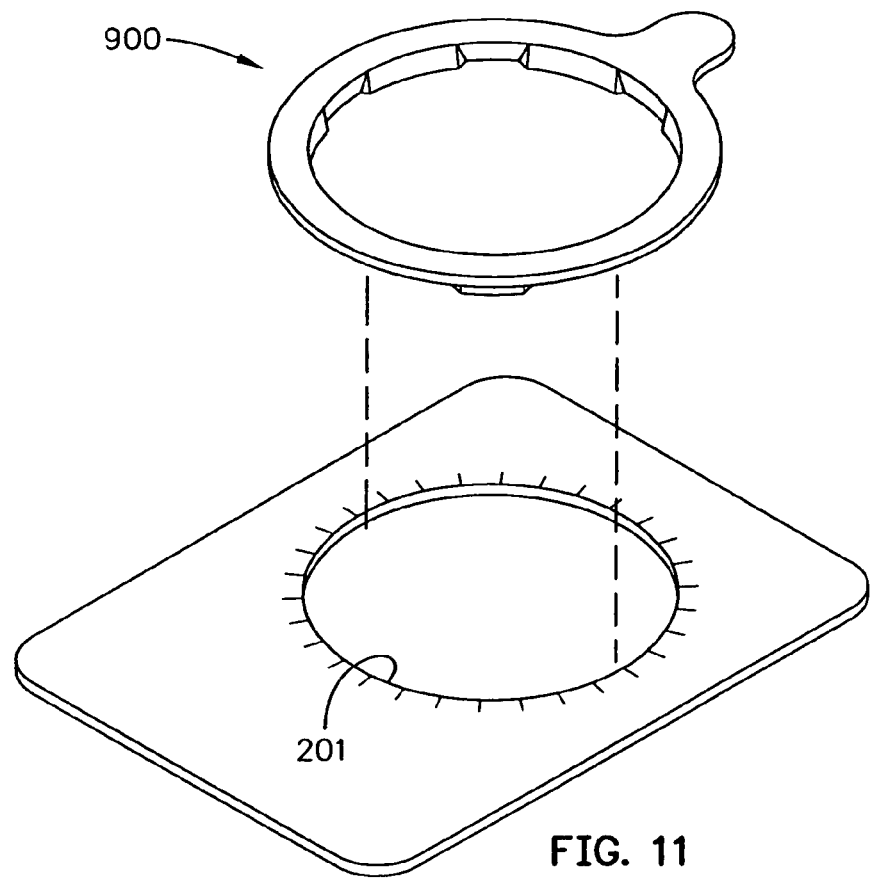
FIG. 11 is an illustration of the embodiment of FIG. 9a suspended over a port.
Figure 12:
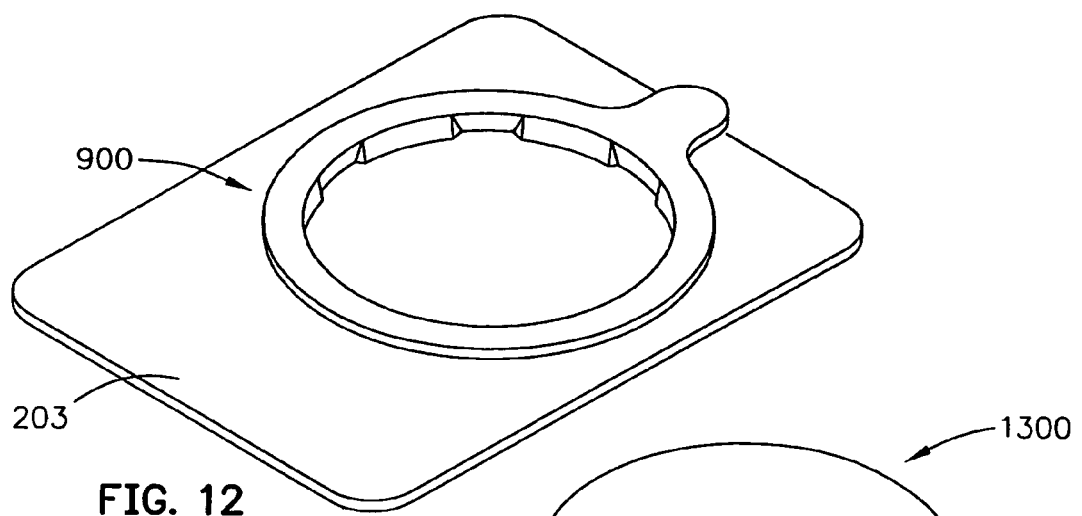
FIG. 12 is an illustration of the embodiment of FIG. 9a inserted in the port.

In one embodiment of the present invention shown in FIG. 9b the protuberances 907 are retractable, and retract along the path indicated by arrow 913. When force is applied against the protuberance 907, an arm 915 flexes. A slit 917 frees the arm 915 from the wall 903 and allows the protuberance 907 to retract. FIG. 11 shows the plug 900 suspended above the port 201 prior to insertion into the port. FIG. 12 illustrates the plug 900 after insertion into the port 201.

Figure 13:
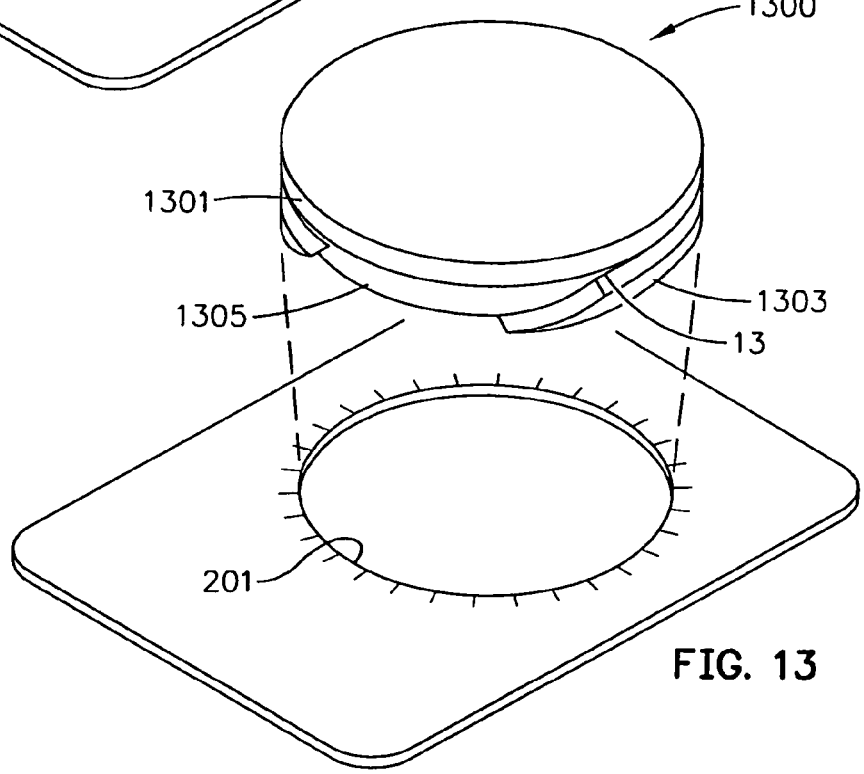
FIG. 13 is an illustration of an embodiment having threads.
Figure 14:
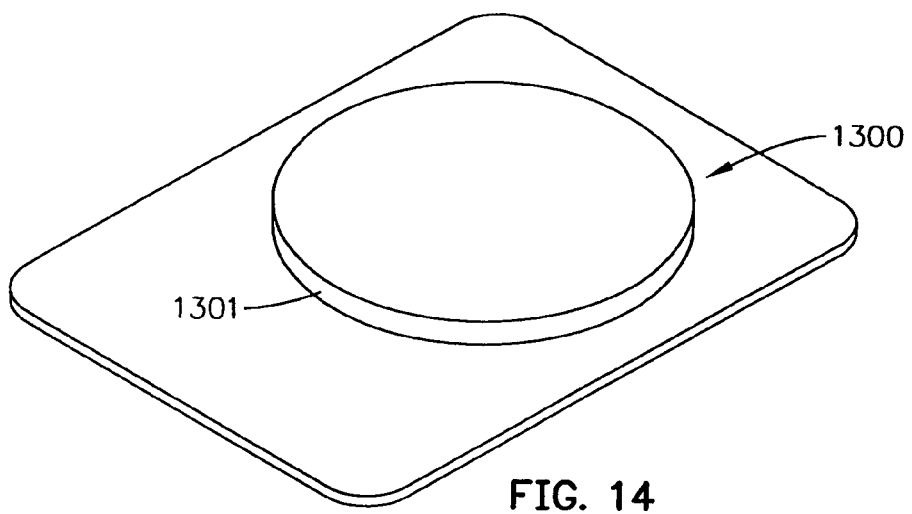
FIG. 14 is an illustration of the embodiment of FIG. 13 after insertion in the port.

FIG. 13 illustrates yet another alternative embodiment to the present invention. The plug 1300 is preferably molded from plastic. The plug 1300 is retained in the port 201 by spiral groves 13 molded/etched into the edges of the plug 1300 to form threads 1303. The plug 1300 may be screwed into the port 201 and later unscrewed from the port 201. The plug 1300 preferably has a flange 1301 which is larger than the port 201. The body 1305 of the plug 1300 preferably has a diameter which is equal to or slightly larger than the diameter of the port 201. FIG. 14 is an illustration of the plug 1300 after insertion into a port 201. Only the flange 1301 is visible in FIG. 14.

Figure 15:
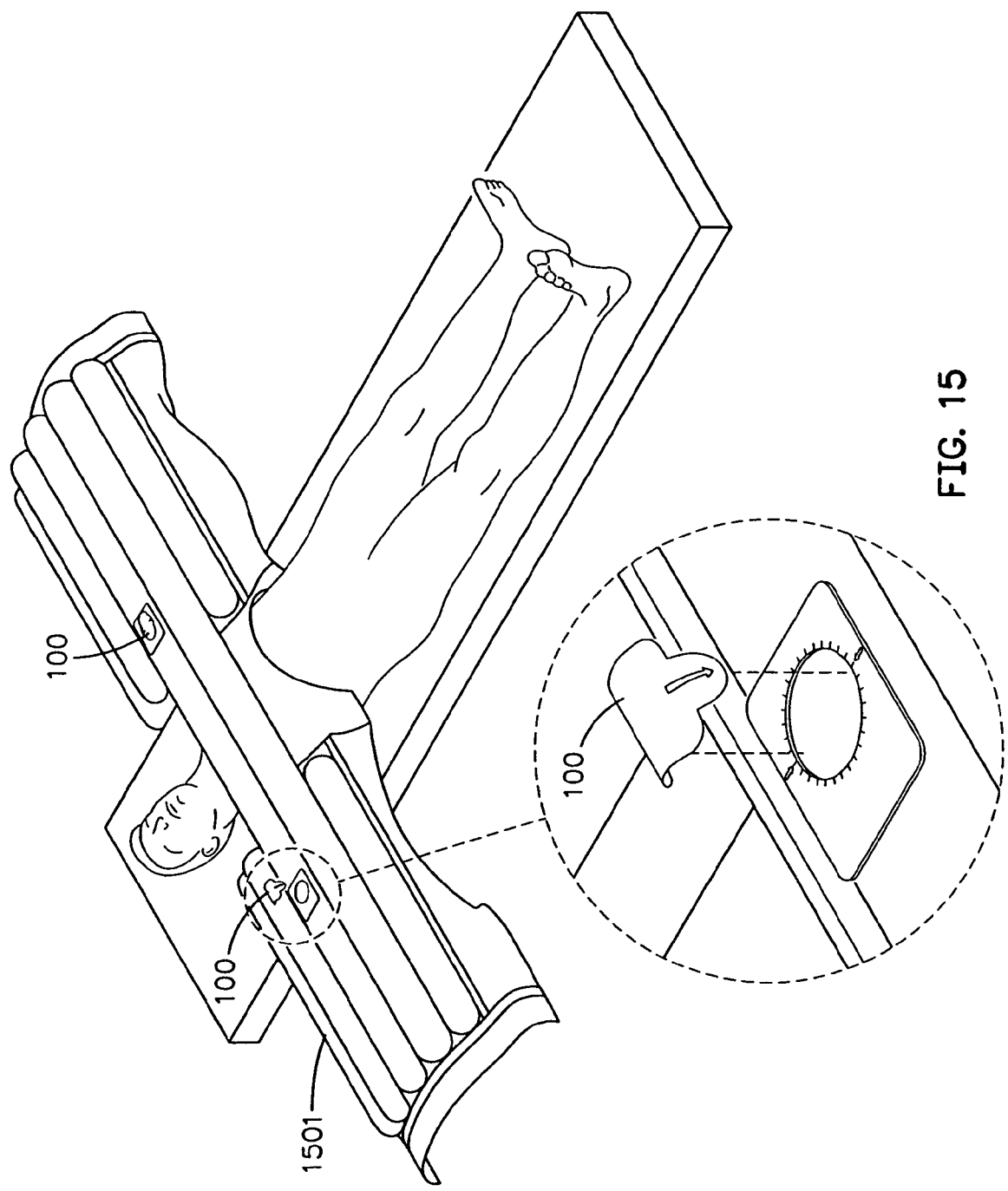
FIG. 15 illustrates the present invention in use with a conventional upper body inflatable thermal blanket.
Figure 16:
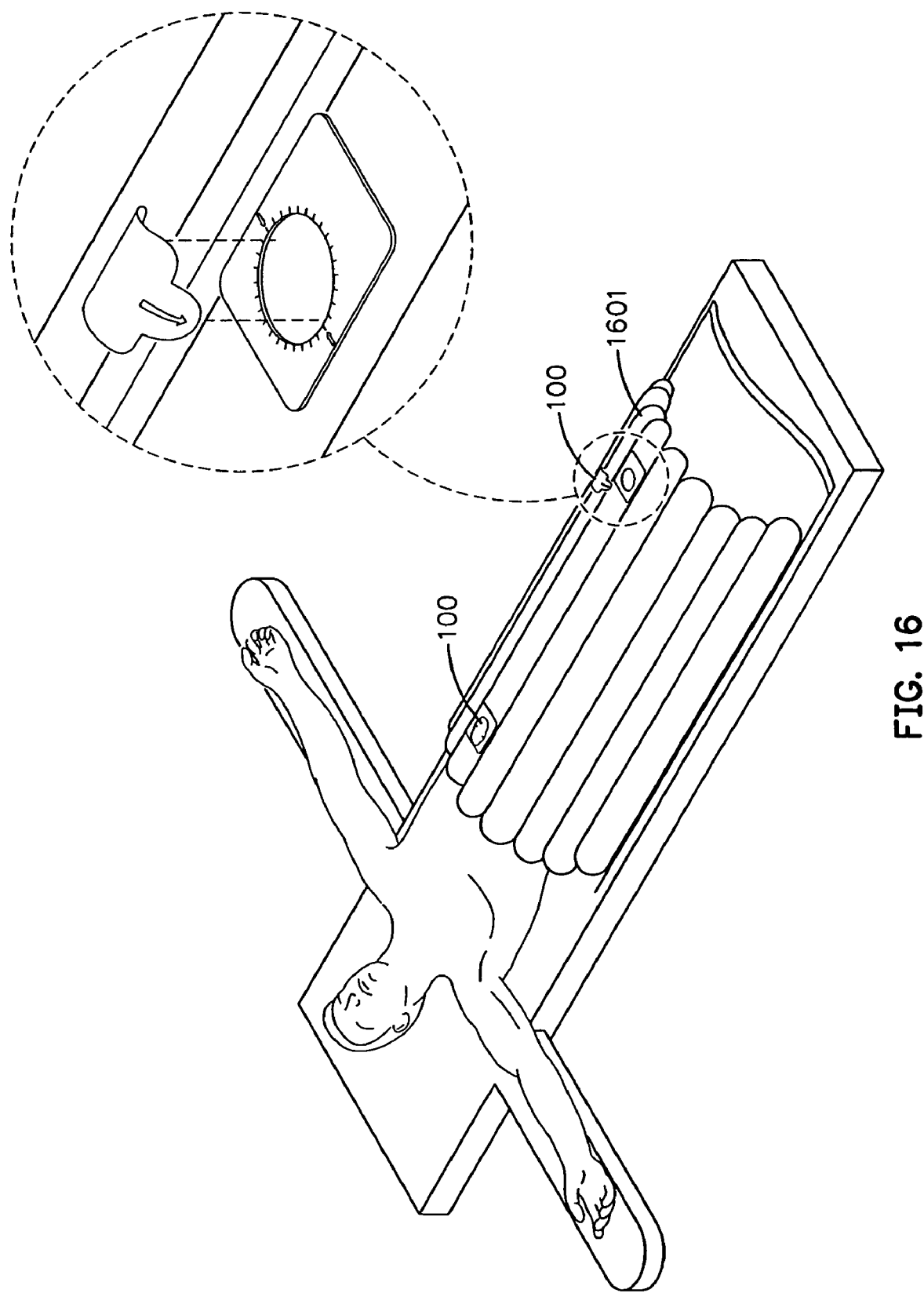
FIG. 16 shows the present invention in use with a lower body inflatable thermal blanket.

FIG. 15 illustrates the inlet port plug 100 in use with a conventional upper body inflatable thermal blanket 1501. FIG. 16 shows the inlet port plug 100 in use with a lower body inflatable thermal blanket 1601. The inlet port plug may generally be used with these and other inflatable thermal blankets.

SUMMARY

A number of embodiments of the present invention have been described. Nevertheless, it will be understood that various modifications may be made without departing from the spirit and scope of the invention. For example, the plugs shown in FIGS. 1-6 may be fabricated from any generally resilient sheet of material.

Furthermore, the nature of the material which defines the inlet port is not critical to the present invention. Accordingly, the sheet which forms the inlet port may be cardboard, plastic metal, ceramic, or any other material. Still further, the protuberances 907 shown in FIGS. 9a-12 may form a single continuous ring about the ring-like vertical wall 903. Still further yet, the angle of the lower and upper slope 909, 911 of the embodiment of the present invention shown in FIGS. 9a-12, may differ substantially from one another. Also, the plug 900 shown in FIGS. 9a-12 may be formed without the tab 905, and the flange may be formed at an angle other than 90° with the vertical wall 903.

Accordingly, it is to be understood that the invention is not to be limited by the specific illustrated embodiment, but only by the scope of the appended claims.

The invention claimed is:

1. An apparatus for warming a person, comprising:
   an inflatable cover for disposition on a portion of a person's body;
   two inlet ports in the inflatable cover; and,
   a plug removably received in at least one inlet port of the two inlet ports;
   the plug including:
   a planar central body; and,
   a plurality of non-curved extensions coplanar with the central body and which extend from the central body, at least two of which are receivable in the one inlet port.

2. The apparatus of claim 1 wherein at least one of the extensions is triangular.

3. The apparatus of claim 1 wherein at least one of the extensions is rectangular.

4. The apparatus of claim 1 wherein at least one of the extensions has a distal end which is notched.

5. The apparatus of claim 1 wherein the plurality of extensions includes three pairs of opposing extensions.

6. The apparatus of claim 1, wherein:
   the first inlet port includes a first sheet of flexible material attached to the inflatable cover and a hole adapted to receive the nozzle of an air hose; and
   the second inlet port includes a second sheet of flexible material attached to the inflatable cover and a hole adapted to receive the nozzle of an air hose.

7. The apparatus of claim 6 wherein at least one of the extensions is triangular.

8. The apparatus of claim 6 wherein at least one of the extensions is rectangular.

9. The apparatus of claim 6 wherein at least one of the extensions has a distal end which is notched.

10. The apparatus of claim 6 wherein the plurality of extensions includes three pairs of opposing extensions.

* * * * *

UNITED STATES PATENT AND TRADEMARK OFFICE
CERTIFICATE OF CORRECTION

PATENT NO.        : 7,587,837 B2                                          Page 1 of 1
APPLICATION NO. : 11/818721
DATED             : August 25, 2009
INVENTOR(S)       : Arnold et al.

It is certified that error appears in the above-identified patent and that said Letters Patent is hereby corrected as shown below:

Title Page, item [56]
Under the heading U.S. PATENT DOCUMENTS
  column 2, line 6, replace "3,829,918 A 8/1974 Stamberger" with "3,829,918 A 8/1974 Stamberger 5/348".
  column 2, line 7, replace "3,978,530 A 9/1976 Amarantos" with "3,978,530 A 9/1976 Amarantos 5/68".
  column 2, line 10, replace "4,086,670 A 5/1978 Krause et al." with "4,086,670 A 5/1978 Krause et al. 4/295".
  column 2, line 14, replace "4,930,174 A 6/1990 Hunter" with "4,930,174 A 6/1990 Hunter 5/454".
  column 2, line 15, replace "5,000,663 A 3/1991 Gorton" with "5,000,663 A 3/1991 Gorton 417/63".
  column 2, line 17, replace "5,075,910 A 12/1991 Morten" with "5,075,910 A 12/1991 Morten 5/53.1".

Column 3, line 23
Delete the word "essential" and replace it with the word "essentially".

Column 4, line 44
Delete the word "filly" and replace it with the word "fully".

Signed and Sealed this

Fifth Day of January, 2010

David J. Kappos
*Director of the United States Patent and Trademark Office*

UNITED STATES PATENT AND TRADEMARK OFFICE
CERTIFICATE OF CORRECTION

PATENT NO. : 7,578,837 B2  Page 1 of 1
APPLICATION NO. : 11/818721
DATED : August 25, 2009
INVENTOR(S) : Arnold et al.

It is certified that error appears in the above-identified patent and that said Letters Patent is hereby corrected as shown below:

Title Page, item [56]
Under the heading U.S. PATENT DOCUMENTS
    column 2, line 6, replace "3,829,918 A 8/1974 Stamberger" with "3,829,918 A 8/1974 Stamberger 5/348".
    column 2, line 7, replace "3,978,530 A 9/1976 Amarantos" with "3,978,530 A 9/1976 Amarantos 5/68".
    column 2, line 10, replace "4,086,670 A 5/1978 Krause et al." with "4,086,670 A 5/1978 Krause et al. 4/295".
    column 2, line 14, replace "4,930,174 A 6/1990 Hunter" with "4,930,174 A 6/1990 Hunter 5/454".
    column 2, line 15, replace "5,000,663 A 3/1991 Gorton" with "5,000,663 A 3/1991 Gorton 417/63".
    column 2, line 17, replace "5,075,910 A 12/1991 Morten" with "5,075,910 A 12/1991 Morten 5/53.1".

Column 3, line 23
Delete the word "essential" and replace it with the word "essentially".

Column 4, line 44
Delete the word "filly" and replace it with the word "fully".

This certificate replaces the Certificate of Correction issued on January 5, 2010 which contained a typographical error in the patent number. The patent number was incorrectly given as 7,587,837. The corrections in the January 5, 2010 Certificate of Correction belonged to Patent No. 7,578,837. This certificate supersedes the Certificate of Correction issued January 5, 2010.

Signed and Sealed this

Twenty-ninth Day of June, 2010

David J. Kappos
*Director of the United States Patent and Trademark Office*